(12) United States Patent
Reever et al.

(10) Patent No.: US 8,105,317 B2
(45) Date of Patent: Jan. 31, 2012

(54) URETHRAL SEALING METHOD AND DEVICE

(75) Inventors: Kenneth Reever, Hopedale, MA (US); Jozef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 971 days.

(21) Appl. No.: 10/929,671

(22) Filed: Aug. 30, 2004

(65) Prior Publication Data

US 2006/0047269 A1    Mar. 2, 2006

(51) Int. Cl.
*A61M 27/00* (2006.01)
*A61M 1/00* (2006.01)
*A61M 5/32* (2006.01)

(52) U.S. Cl. ......... 604/544; 604/540; 604/265; 604/266

(58) Field of Classification Search .............. 600/29–32; 623/23.66, 23.65, 23.67, 22.66; 604/540, 604/544, 103.03; 606/193
See application file for complete search history.

(56) References Cited

U.S. PATENT DOCUMENTS

| | | | | |
|---|---|---|---|---|
| 2,822,809 A * | 2/1958 | Sollmann | .................. | 604/278 |
| 3,951,153 A * | 4/1976 | Leucci | .................. | 604/544 |
| 4,044,401 A * | 8/1977 | Guiset | .................. | 623/23.65 |
| 4,324,262 A * | 4/1982 | Hall | .................. | 600/569 |
| 4,555,242 A * | 11/1985 | Saudagar | .................. | 604/103.08 |
| 4,781,176 A * | 11/1988 | Ravo | .................. | 600/30 |
| 4,799,928 A * | 1/1989 | Crowley | .................. | 604/329 |
| 4,893,621 A * | 1/1990 | Heyman | .................. | 606/127 |
| 5,049,140 A * | 9/1991 | Brenner et al. | .................. | 604/266 |
| 5,300,022 A * | 4/1994 | Klapper et al. | .................. | 604/35 |
| 5,505,695 A * | 4/1996 | Eplett, Jr. | .................. | 604/544 |
| 5,713,861 A | 2/1998 | Vanarthos et al. | | |
| 5,902,337 A | 5/1999 | Di Lelio et al. | | |
| 6,090,069 A * | 7/2000 | Walker | .................. | 604/102.03 |
| 6,296,668 B1 | 10/2001 | Desgrandchamps et al. | | |
| 6,746,421 B2 * | 6/2004 | Yachia et al. | .................. | 604/93.01 |
| 2002/0188246 A1 | 12/2002 | Hayner et al. | | |
| 2003/0149489 A1 * | 8/2003 | Stark et al. | .................. | 623/23.66 |

FOREIGN PATENT DOCUMENTS

WO    95/11637        5/1995
WO    03/094784 A2   11/2003

OTHER PUBLICATIONS

Answers.com, definition of "channel", www.answers.com/topic/channel.*

* cited by examiner

*Primary Examiner* — Leslie Deak
*Assistant Examiner* — Susan Su
(74) *Attorney, Agent, or Firm* — Brown Rudnick LLP (57) ABSTRACT

An urethral sealing device comprising first and second body portions selectively attacheable to one another to form a unitary element including a first catheter lumen extending therethrough between proximal and distal ends of the unitary element wherein, when the sealing device is in an operative position, the distal end is positioned within a urinary bladder and a sealing element extending radially outward from the unitary element so that, when the sealing device is in the operative position, the sealing element engages one of a wall of the urethra and a wall of the urinary bladder around an orifice at which the urethra opens into the urinary bladder to seal the urethra.

16 Claims, 12 Drawing Sheets

URETHRAL SEALING METHOD AND DEVICE

BACKGROUND

Interstitial cystitis (IC) is a chronic inflammation or irritation of the urinary bladder wall with symptoms including urinary urgency, frequency, and often-severe pelvic and perineal pain which are similar to those of other bladder diseases, such as urinary tract infections (UTI), urethritis, urethral syndrome, trigonitis, prostatitis, dysuria, and nocturia. Thus diagnosis of the IC is difficult. After other similar bladder diseases have been ruled out a cystoscopic examination of the bladder wall may be carried out. If this examination reveals small petechial hemorrhages or larger Hunner's Ulcers, IC is usually diagnosed.

The cause of IC remains undetermined. Theories linking IC to bacterial infections are controversial as IC patients routinely test negative for infection in standard urinalysis. However, several studies have shown that symptoms are alleviated when IC patients are treated with antibiotics. Other theories point to defects in the epithelial permeability barrier of the bladder surface glycosaminoglycans (GAG). Once the bladder wall has lost the protective coating of GAG, irritative components and potentially pathogenic bacteria may lead to the inflammation or irritation associated with IC. Another line of research indicates that activated mast cells associated with pain and irritation are involved in the pathology of IC. Studies have shown that IC patients have an increased level of activated mast cells in tissues of their bladder walls.

Currently there is no treatment which permanently eliminates the symptoms of IC in the majority of patients. Drug therapy has been proven to be the most effective means of alleviating symptoms. Oral medications for IC include bladder-coating agents, antidepressants, antihistamines, antispasmodics and anesthetics. The effectiveness of oral medications is limited by the circulating concentration of the drug in the blood stream. To address this limitation, many IC patients elect to undergo a procedure called urinary bladder instillation, in which a therapeutic solution is pumped into the bladder through a urethral catheter. The solution, which may be composed of one medicine or a combination of medications, is held in the bladder for a "dwell time" before the bladder is voided. This procedure allows the treatment of the urinary bladder wall directly with high concentrations of medicine. Despite the drawbacks of a limited dwell time for the medication to take effect and the resulting mixing of medication with urine, bladder instillation remains among the most effective conventional treatments for IC.

SUMMARY OF THE INVENTION

In one aspect, the present invention is directed to a urethral sealing device comprising first and second body portions selectively attacheable to one another to form a unitary element including a first catheter lumen extending therethrough between proximal and distal ends of the unitary element wherein, when the sealing device is in an operative position, the distal end is positioned within a urinary bladder and a sealing element extending radially outward from the unitary element so that, when the sealing device is in the operative position, the sealing element engages one of a wall of the urethra and a wall of the urinary bladder around an orifice at which the urethra opens into the urinary bladder to seal the urethra.

The present invention is further directed to a system for treating a urinary tract, comprising a bladder liner element which, when in an operative position, is inserted in the bladder, an outflow catheter extending from a proximal end of the bladder liner wherein, when in the operative position, the outflow catheter extends into the urethra, a first inflow catheter extending from a distal end of the bladder liner wherein, when in the operative position, the first inflow catheter extends into a first ureter and a first ureter sealing element which, when the first inflow catheter is in the operative position, prevents urine from flowing into the bladder so that urine flows from the first inflow catheter into the bladder liner and through the outflow catheter to pass out of the body.

DETAILED DESCRIPTION

The present invention provides a liner or bypass for the bladder, so that urine is discharged without contacting the walls of the bladder. The bypass or liner may be introduced through the urethra and placed within the bladder. Various configurations of this device will be described below, which are better suited for different patients and applications.

In the course of treating the bladder with the liner according to embodiments of the present invention, it may be necessary to provide a fluid proof seal between the walls of the urethra and the device, as well as between the walls of the two ureters and the device. In particular, the openings of the ureters may be sealed to prevent urine from entering the bladder and the urethra may be sealed to retain medicated fluids introduced into the bladder therein for a desired time. A sealing device may be used at the opening of the bladder into the urethra to prevent such fluids from leaking out prematurely.

Figure 1:
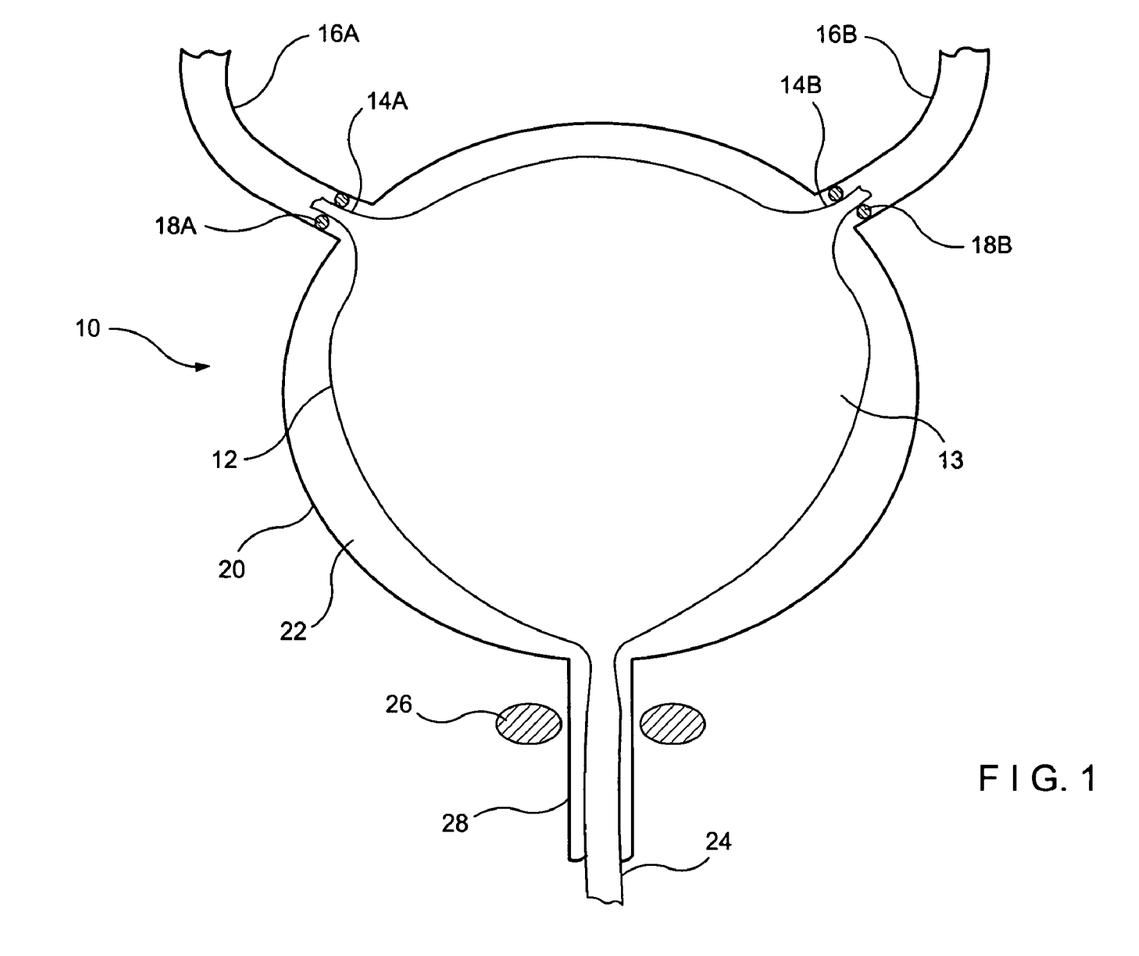
FIG. 1 is a schematic drawing showing a bladder liner with three openings designed to fit inside a patient's urinary bladder according to an embodiment of the invention.

FIG. 1 depicts an exemplary insert device 10 according to the invention for isolating the wall 20 of the urinary bladder from contact with urine. Urine normally flows from the kidneys into the ureters 16A,B, which drain into the urinary bladder where it is held until the urinary sphincter 26 relaxes. This allows urine to flow from the bladder through the urethra 28 and out of the body. The insert device 10 collects the urine entering the urinary bladder via the ureters 16A,B and prevents contact between the urine and the bladder wall 20. Isolating the bladder wall 20 from the urine confers therapeutic benefits in the treatment of bladder diseases, infections, and disorders. Specifically, isolating the bladder wall 20 from urine allows medications introduced within a space 22 between the bladder wall 20 and a liner 12 of the device 10 to function more effectively. It also allows the bladder wall 20 to be treated with medications introduced into the space 22 without the medications being diluted by urine. Thus, the strength of the medications is maintained and the medications are not flushed out of the body too soon following the voiding of the bladder.

Urine is known to have a strong caustic effect on cells. In a healthy bladder, specialized epithelial cells line the surface of the wall 20 and are well adapted to survive the caustic environment that urine creates. Isolating urine from the urinary bladder provides a relatively non-caustic environment that allows epithelial cells that have been damaged or which are in a diseased state to better recover from disease or to fight infection. The healing of the diseased inner wall of a patient's bladder is thus greatly facilitated and expedited by use of the liner device 10.

In the exemplary embodiment of the invention shown in FIG. 1, a liner 12 designed to fit inside the bladder is constructed, for example, from an impermeable but highly flexible and elastic material. The liner 12 forms a reservoir 13 in which urine is collected. Materials suitable for the liner 12 include, for example, vinyl, polyethylene, PVC, latex, silicone, ethylene vinyl acetate, and polypropylene. The liner 12 is preferably constructed with two inlet orifices 14A,B adapted to sealably connect to the openings of the respective ureters 16A,B. The seals 18A,B between the ureters 16A,B and inlet orifices 14A,B prevent urine from leaking around the orifices 14A,B into the space 22 between the wall 20 of the bladder and the liner 12.

The outlet orifice 24 of the liner 12 is adapted to extend into the urethra 28, directing the flow of urine through the urethra 28 and out of the body without contacting the surrounding tissue. The outlet orifice 24 of this exemplary embodiment is shown extending past the urinary sphincter 26. However, the outlet orifice 24 does not have to extend past the urinary sphincter 26 so long as the outlet orifice 24 is located in such a way as to prevent backflow of urine into the bladder. The exemplary liner device 10 allows the sphincter 26 to maintain normal function during the treatment, which improves patient tolerance for the procedure.

Figure 2:
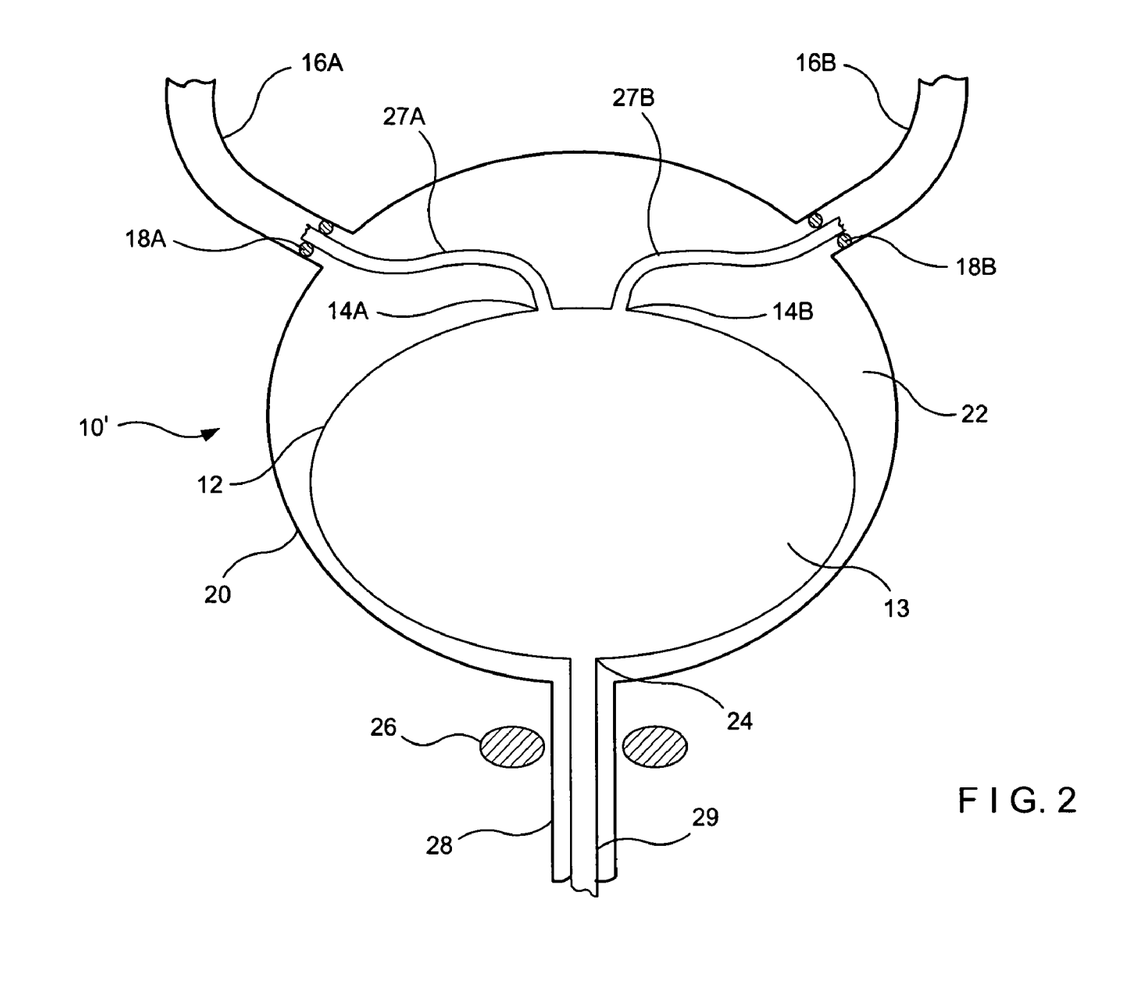
FIG. 2 is a schematic drawing showing of a bladder liner with three catheters designed to fit inside a patient's urinary bladder according to a second embodiment of the invention.

Another exemplary embodiment of the invention is shown in FIG. 2. In this embodiment, the liner device 10' comprises a liner 12 designed to fit inside the urinary bladder. The liner 12 is preferably constructed from a substantially impermeable material, as described above and includes a reservoir 13 formed therein. In the device 10' of FIG. 2, each of two inlet orifices 14A,B is connected directly to a respective one of two inlet catheters 27A,B. The inlet orifices 14A,B and the catheters 27A,B may be joined by use of a fitting or any suitable bonding process known in the art. In an operative position, the open ends of the two catheters 27A,B are sealably connected to the openings of the respective ureters 16A,B. As would be understood by those skilled in the art, the sealing of the catheters 27A,B within the ureters 16A,B may be accomplished through mechanical means, such as with the use of bio-adhesives, o-ring(s), or soft radial fins extending from the catheters. The seals 18A,B may be disposed between the ureters 16A,B and the corresponding input catheters 27A,B to prevent urine from leaking into the space 22 and to ensure the flow of urine into the liner 12. Suitable bioadhesives which may be employed in the seals 18A,B and 31 (described below) include fibrin glue, cynoacrylates, and collagen cuffs. Additional conventional methods of sealing a catheter to a biological tissue may be employed, as will be understood to those of skill in the art.

An outlet catheter 29 is connected to the outlet orifice 24 of the bladder liner 12 and, in the operative position, extends through the urethra 28 to direct the flow of urine through the urethra 28 and out of the body. In this exemplary embodiment, the outlet catheter 29 extends into the urethra 28 beyond the location in the urethra that is constricted by the urinary sphincter 26. The outlet catheter 29 is preferably composed of a material sufficiently flexible so that the catheter 29 can be completely compressed by the urinary sphincter 26 to prevent incontinence and to improve patient comfort.

Figure 3:
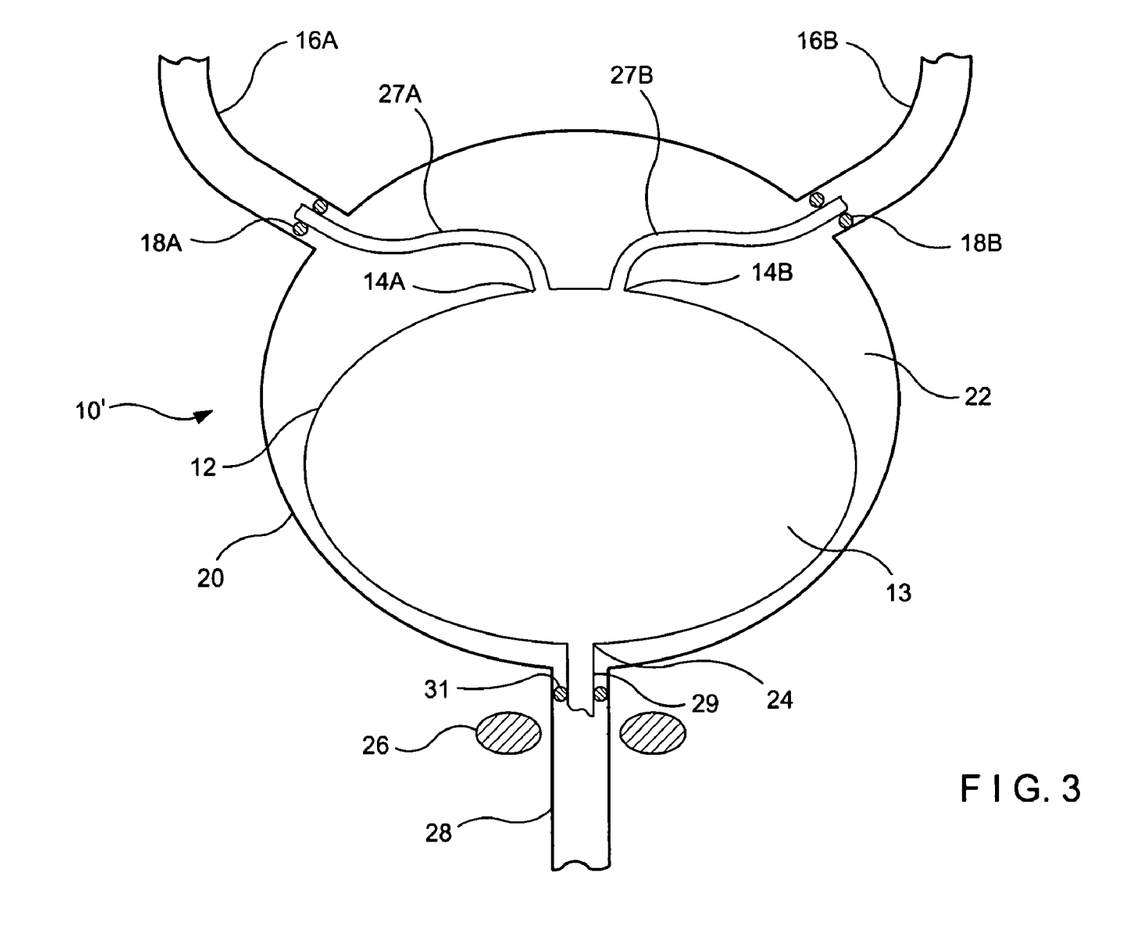
FIG. 3 is a schematic drawing showing a bladder liner with three catheters designed to fit inside a patient's urinary bladder and which includes a seal in the patient's urethra according to a third embodiment of the invention.

An alternative embodiment of the liner device according to the invention is shown in FIG. 3. Here, the outlet catheter 29 is adapted to sealably connect to the wall of the urethra 28 above the location in the urethra 28 that is constricted by the urinary sphincter 26. The catheter 29 may be sealably connected to the urethra using bioadhesives or one or more o-ring(s) 31 as described above in regard to the seals 18A,B. In other embodiments, the seals may comprise radial fins, balloons and/or collagen cuffs disposed around the catheter 29 at an appropriate longitudinal position. As discussed above, the connections between the ureters 16A,B and the upper input catheters 27A,B are also sealable using seals 18A,B as described above.

In several exemplary embodiments of the invention, the sealable connections 18A,B and 31 may be formed by using at least one nonpermanent biocompatible adhesive or sealant. In these applications, the adhesive forms a fluid-impermeable seal that prevents urine from passing through the annular space between the catheters 27A,B and the ureter walls into the space 22 between the wall 20 of the bladder and the liner 12. At the same time, the seals 18A,B and 31 prevent medicated fluids introduced into the space 22 from exiting the bladder.

Figure 4:
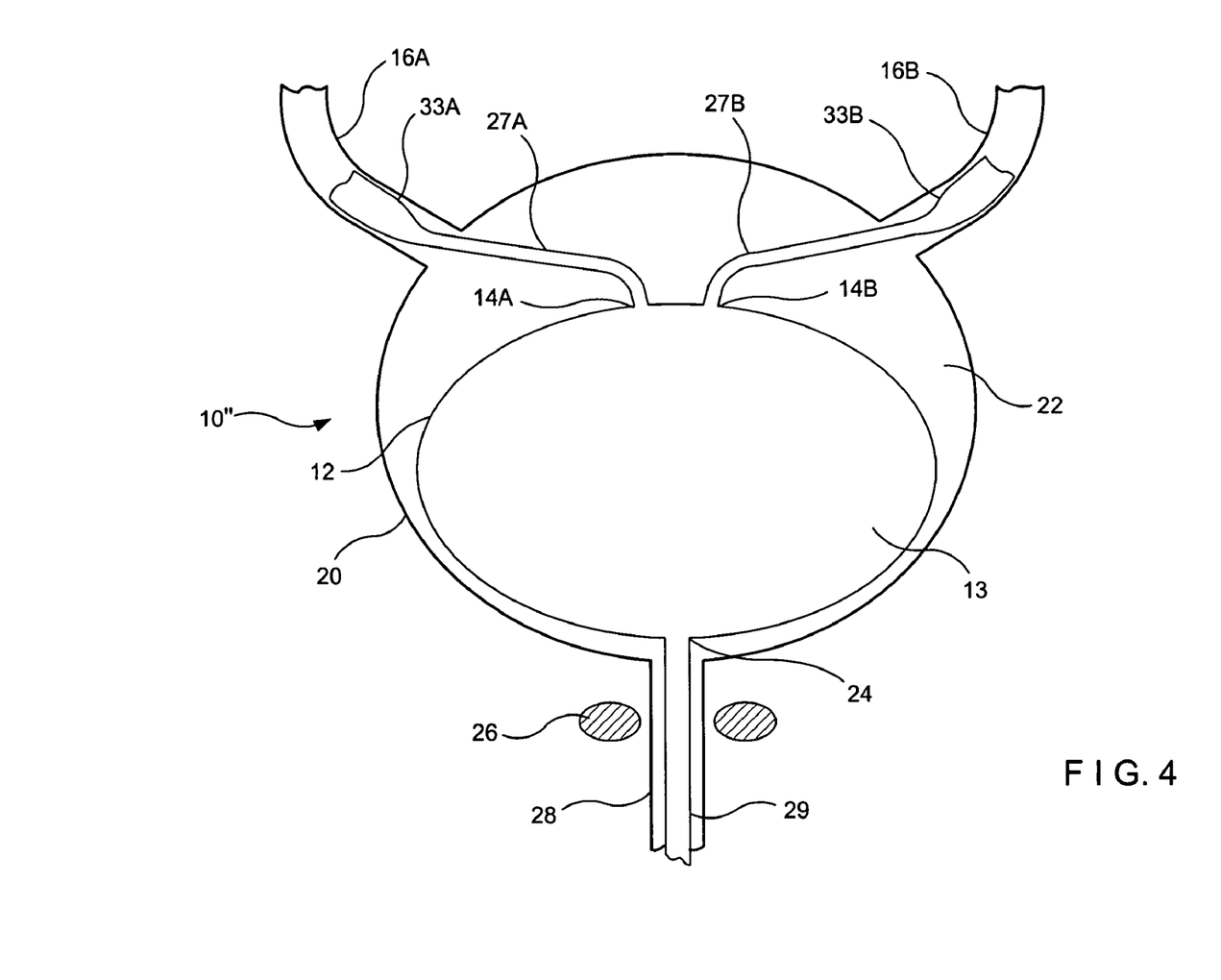
FIG. 4 is a schematic drawing showing a bladder liner designed to fit inside a patient's urinary bladder, having two catheters insertable in the patient's ureters which expand to the diameter of the ureter to form a fluid-impervious junction according to another embodiment of the invention.

In an alternative embodiment shown in FIG. 4, sealable connections between the catheters 27A,B and the ureter walls are produced by expanded diameter distal portions 33A,B of the catheters 27A,B which press outward against the ureter walls to form a fluid tight seal. The catheters 27A,B are held in place in the ureters 16A,B by the mechanical force exerted by the expanded ends 33A,B of the catheters on the surrounding biological tissues. Those skilled in the art will recognize that a similar seal may be formed between the catheter 29 and the wall of the urethra by inclusion of an expanded diameter portion of the catheter 29 which, when in an operative position, is located adjacent to a portion of the urethra where a seal is desired. The exemplary connection used in the insert device 10" thus provides both a liquid-impermeable seal as well as a mechanical connection which holds the catheters in place within the patient's body.

Figure 5:
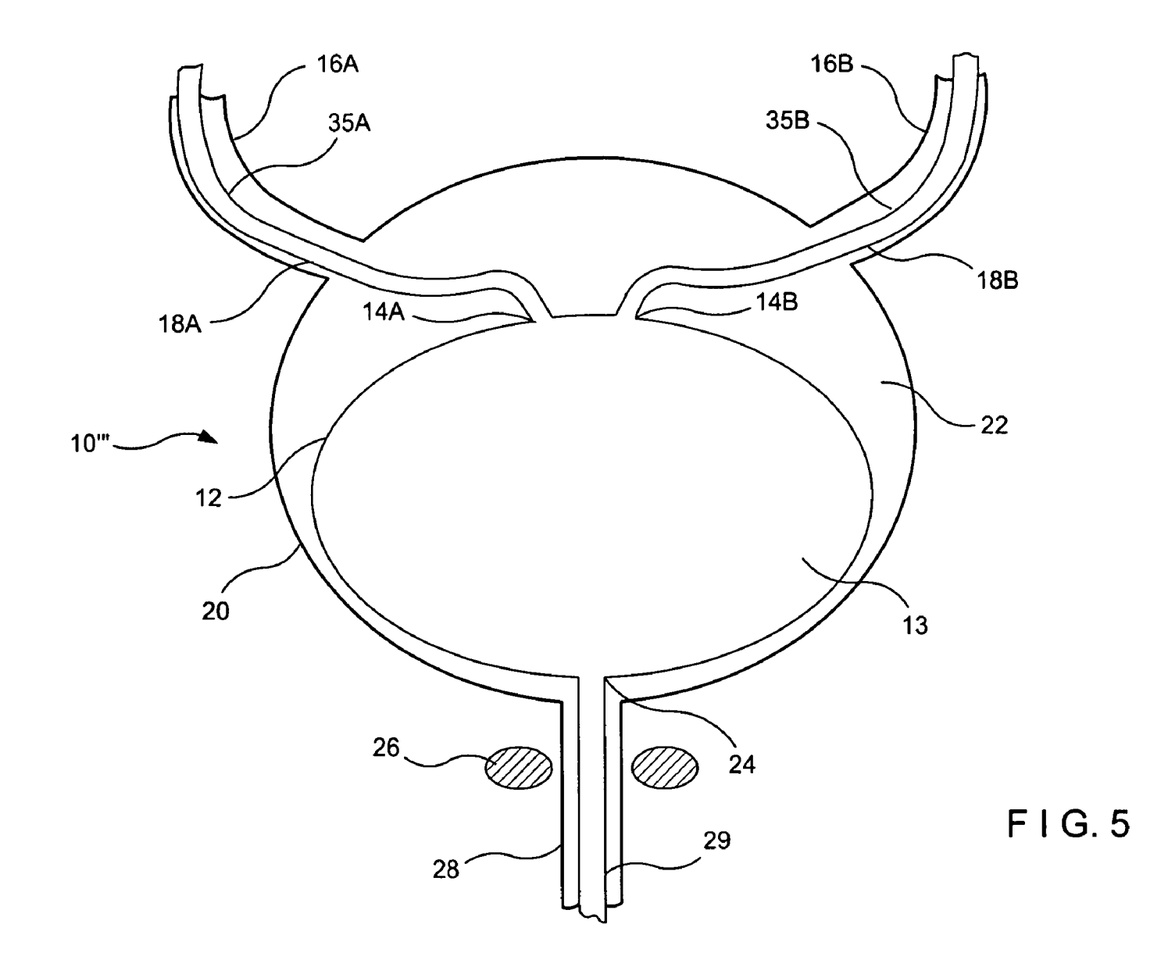
FIG. 5 is a schematic drawing showing a bladder liner designed to fit inside a patient's urinary bladder, with two catheters which extend to the patient's two kidneys according to a different embodiment of the invention.
Figure 6:
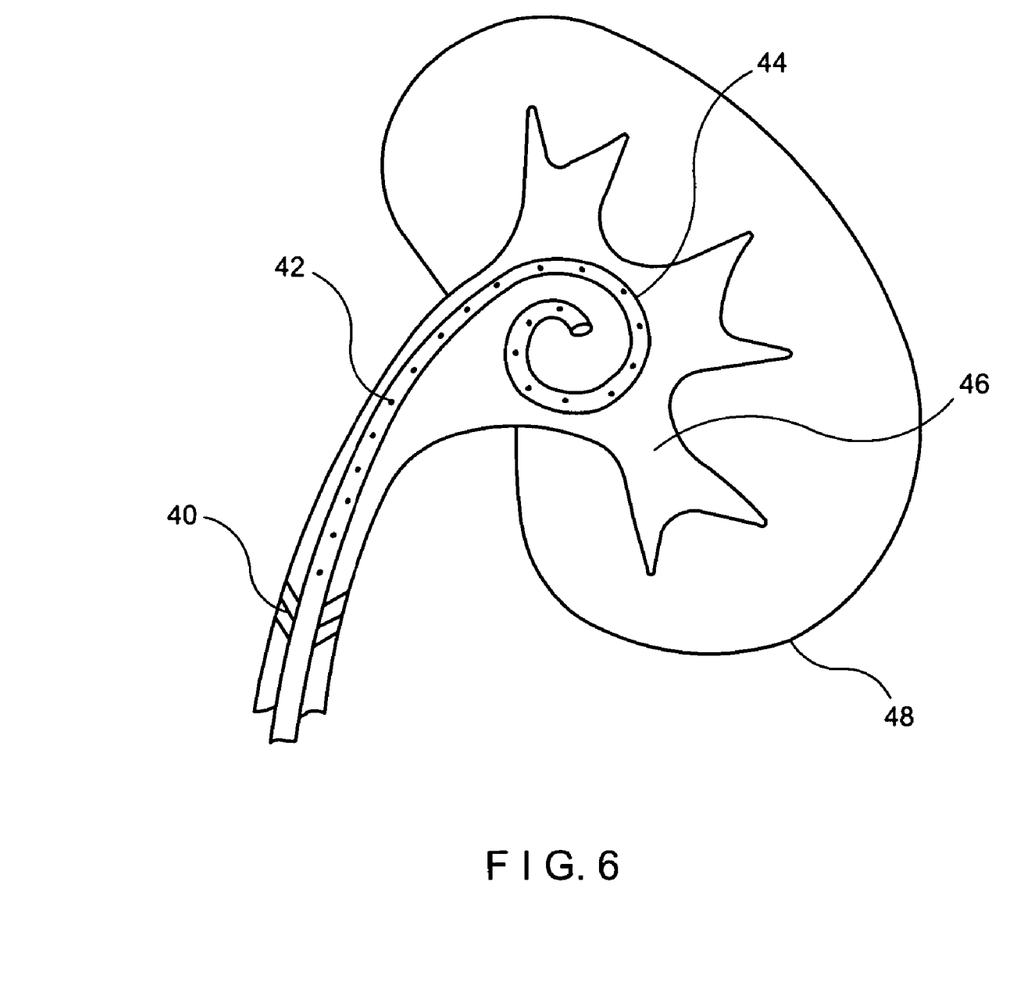
FIG. 6 is a schematic drawing of the bladder liner shown in FIG. 5.

An additional exemplary embodiment of the insert device according to the present invention is shown in FIGS. 5 and 6. In this embodiment, a liner device 10'''comprises a liner 12 made from an impermeable but highly flexible and elastic material, designed to fit inside the urinary bladder. The liner 12 includes a reservoir 13 formed therein and may include two catheters 35A,B connected to inlet orifices 14A,B of the bladder liner 12. The catheters 35A,B extend up the respective ureters 16A,B and into the kidneys 48. FIG. 6 depicts distal portions of the catheters 35A,B which may, for example, each of which comprises a coil 44 which prevents the catheters 35A,B from migrating back down the ureters 16A,B towards the bladder. In addition, the distal portions of each of the input catheters 35A,B preferably posseses a plurality of drainage holes 42, so that the urine formed in the kidneys 48 can easily enter the catheters 35A,B. Proximally of the drainage holes 42, the catheters 35A,B may be fitted with a plurality of fins 40 mounted on the exterior surfaces of the catheters 35A,B which form liquid-impermeable seals with the ureter walls. The fins 40 are preferably constructed out of a soft, flexible material, allowing them to be simply pushed against the ureter walls to form liquid-impermeable seals. The liner 12 may also be constructed with an outlet catheter 29 connected to an outlet orifice 24 of the liner 12. The outlet catheter 29 may include any of the features of the catheters 29 described above to direct the flow of urine through the urethra 28 and out of the body.

In different embodiments according to the invention, the urinary bladder liner 12 may be constructed of either a non-elastic material or of a highly flexible and pliant material. However, it may be necessary to wrap a non-elastic bladder liner around a catheter 35A, B prior to insertion. A non-elastic bladder liner 12 will not expand to the dimensions of the urinary bladder, and thus will not apply pressure to the urinary bladder wall 20 when the bladder liner 12 is filled to or near to its capacity. Alternatively, the liner 12 may be constructed of a highly flexible, pliant material allowing the liner 12 to expand to the dimensions of the urinary bladder. The preferred material to construct the liner according to the invention may be selected depending on the bladder condition to be treated, the condition of the patient, and on the medical infrastructure available for the procedure, among other variables.

The exterior surface of the urinary bladder liner 12 according to the various embodiments presented herein may be coated with heparin or a heparin-like drug to promote the healing of the bladder wall 20 at points where the bladder wall 20 and the bladder liner 12 make contact. In addition, the exterior surface of the urinary bladder liner 12 may be coated with a low friction material such as, for example, a hydrogel to reduce chafing or irritation of the bladder wall 20 at points where the bladder wall 20 and the bladder liner 12 make contact. These points may be subject to rubbing due to movements of the patient over extended periods of time, and thus require special handling to prevent complications from developing as a result of the procedure. Known methods may be used to embed in the outer surface of the bladder liner 12 the selected substances, as a simple coating or a time release type of coating, depending on the desired application.

Figure 7:
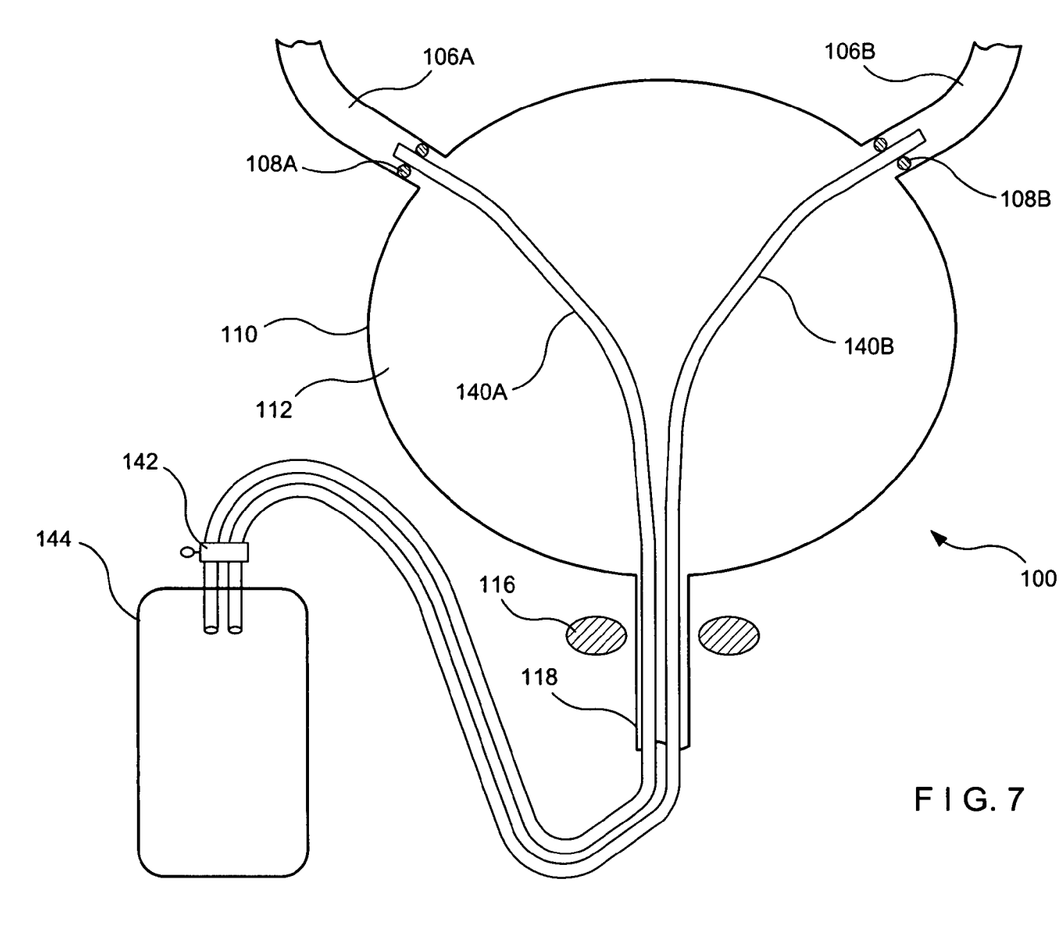
FIG. 7 is a schematic drawing showing a bladder bypass designed to fit inside a patient's urinary bladder, having two catheters attached to the patient's two ureters and extending through the urinary bladder and the urethra to an external urine container, according to an embodiment of the invention.

Another embodiment of a device in accordance with the present invention is shown in FIG. 7. In this case, the device forms a bypass of the patient's bladder, so that the urine formed in the kidneys does not dwell in the bladder, but rather is discharged out of the patient's body through the bypass device 100. Two catheters 140A,B are inserted into the two openings of the ureters 106A,B in the urinary bladder 112 and are sealably connected to the ureter walls as described above in regard to the seals 18A,B. The two catheters 140A,B extend through the urinary bladder 112 and through the urethra 118 to exit the body. As would be understood by those skilled in the art, the catheters 140A,B may lead to an external collection container 144 of conventional design. A valve 142 on each catheter 140A,B may be included to block the flow of urine while removing or replacing the urine collection container 144. Alternatively, a single valve 142 may be used to isolate the flow of urine from each of the catheters 140A,B to the collection container 144. The seals 108A,B used to seal the catheters 140A,B to the ureter 106A,B may comprise bio-compatible adhesive(s), o-ring(s) or fins, and alternatively may comprise portions of the catheters that expand to press against the wall of the ureters 106A,B as described above.

Figure 8:
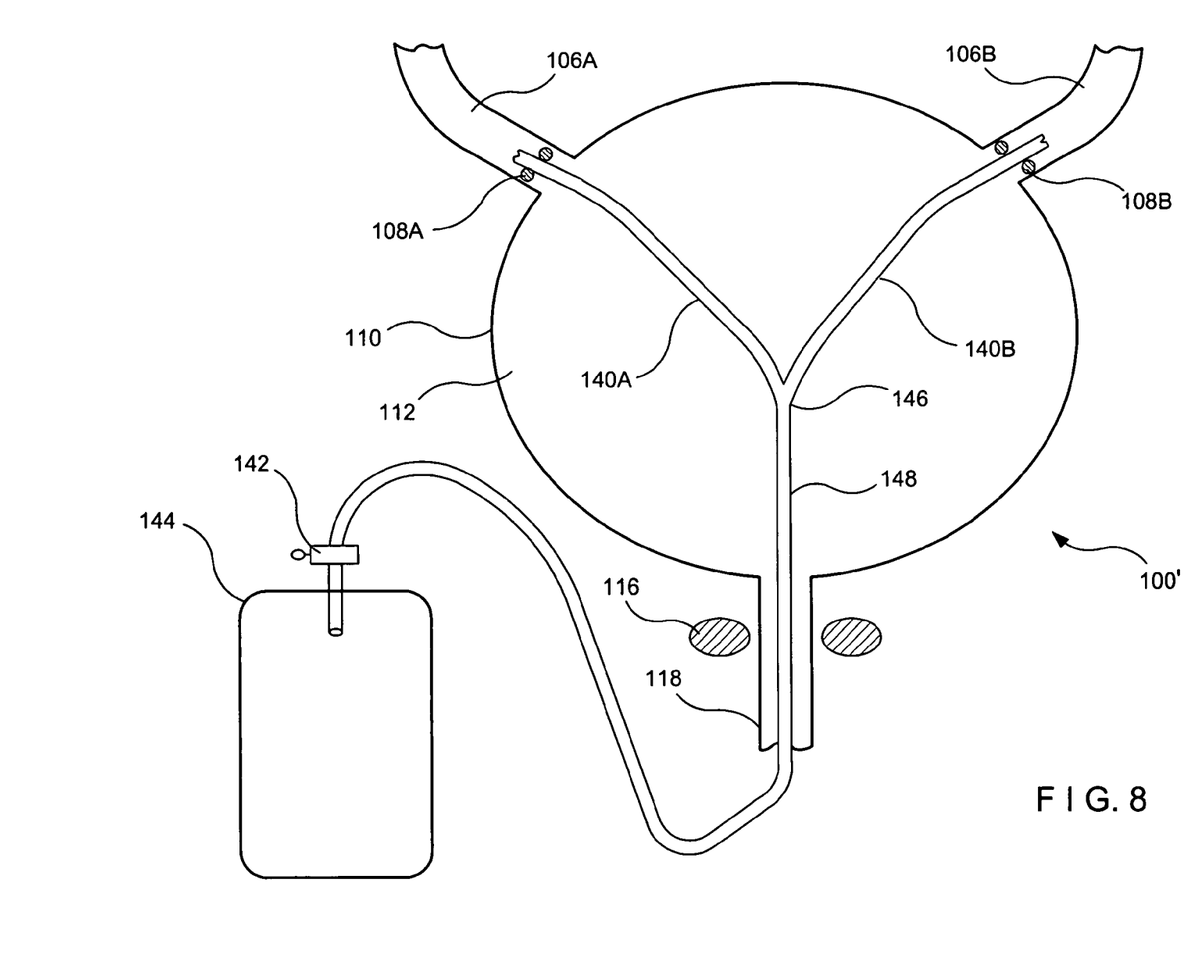
FIG. 8 is a schematic drawing showing a bladder bypass designed to fit inside a patient's urinary bladder, having two catheters connected to the patient's ureters and joining to form one outlet catheter, according to another embodiment of the invention.

A different embodiment represented by the bypass device 100' is shown in FIG. 8. Two catheters 140A,B join in a Y connection to form a third catheter 148 in the urinary bladder 112. The third catheter 148 extends through the urethra 118 and into an external collection container 144. As only the third catheter 148 passes through the urethra 118 during normal functioning of the apparatus, this design provides greater patient comfort. The third catheter 148 may be provided with a valve 142 disposed between the distal end of the urethra 118 and the distal end of the catheter 148, which functions to block the flow of urine while removing or replacing the urine collection container 144. As would be understood by those skilled in the art, the seals 108A,B used to seal the catheters 140A,B to the ureters 106A,B may comprise biocompatible adhesive(s), o-ring(s), or catheter end portions that expand to press against the wall of the ureters 106A,B, as described above. The catheters 140A,B and 148 may be joined at a catheter junction 146 by use of a fitting or bonding, or may be formed as a single assembly, according to conventional methods. The exemplary catheters 140A,B 148 and catheter junction 146 may be formed of materials comprising biocompatible plastics, such as vinyl, polyethylene, PVC, silicone, ethylene vinyl acetate, and polypropylene, among others.

Figure 9:
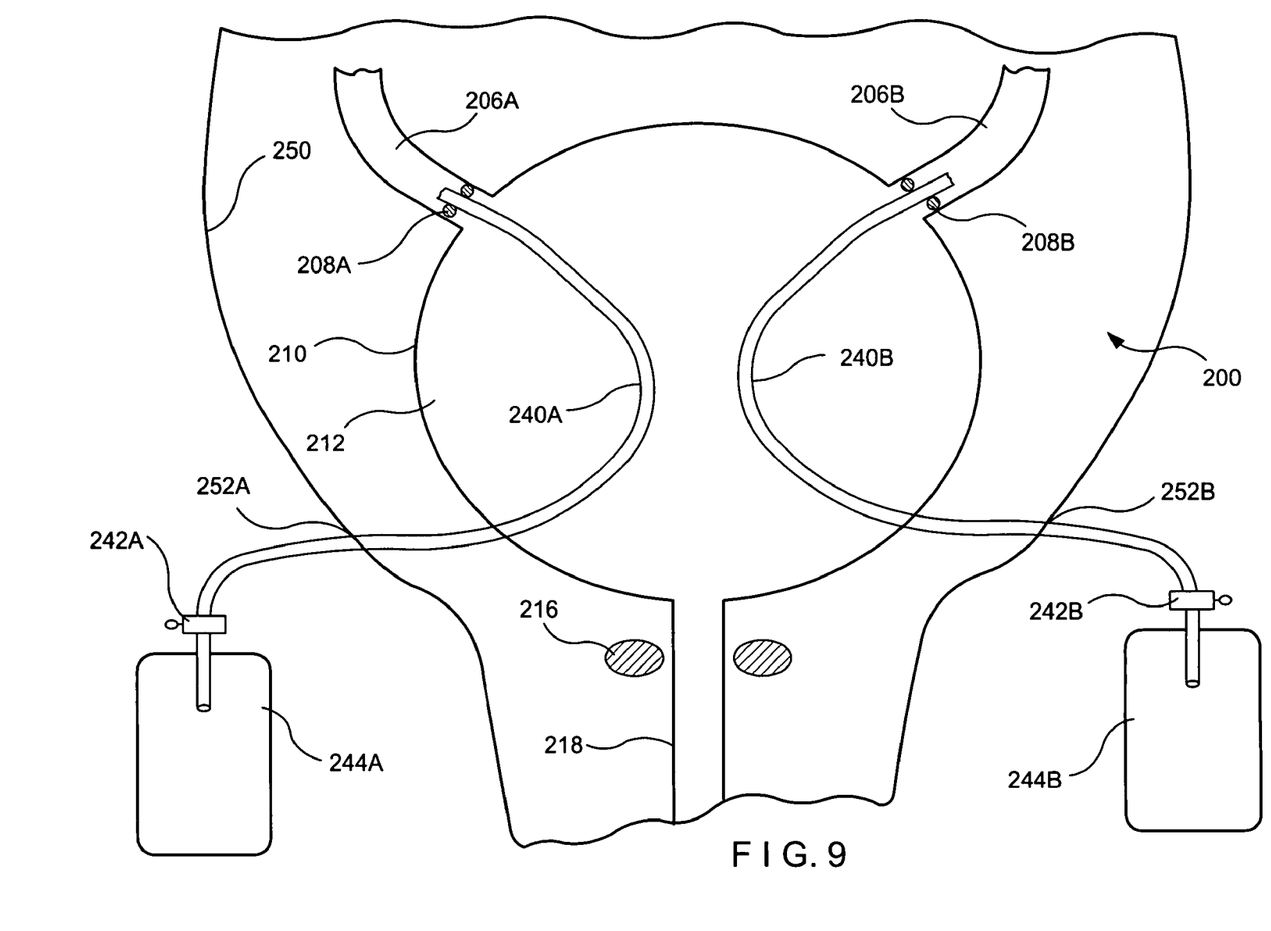
FIG. 9 is a schematic drawing showing a bladder bypass designed to fit inside a patient's urinary bladder, having two catheters connected to the patient's ureters and each extending through a suprapubic incision in the patient's abdominal wall, according to a different embodiment of the invention.

In certain applications, the condition of the patient may make it impractical to direct the outlet catheter(s) through the urinary sphincter and out of the urethra. For those patients, irritation and possible damage to the urethra and sphincter may require an alternate routing for the drainage catheter. FIG. 9 shows an additional exemplary embodiment of a bypass device 200 according to the present invention. Here, each of the catheters 240A,B is inserted into one of the ureters 206A,B and sealed to the ureter walls, as described above. The two catheters 240A,B are extended into the urinary bladder 212, through the bladder wall 210 out of the body via incisions in the abdominal wall 250. Specifically, the catheters 240A,B pass through one or more suprapubic incisions 252A,B surgically formed in the abdominal wall 250, for example, superior to the patient's pubic arch.

This embodiment of a bladder bypass device according to the invention eliminates urine drainage through the urethra 218, thereby eliminating irritation of the urethra 218 and of the urinary sphincter 216 due to the presence of the catheters 240A,B passing therethrough. With no catheters 240A,B present in the urethra 218, the urinary sphincter 216 is allowed to function normally, thus providing greater comfort to the patient. Each one of the catheters 240A,B leads into an external collection container 244A,B. A valve 242A,B may be provided on each catheter 240A,B to block the flow of urine while removing or replacing the urine collection container 244A,B. This may be done in a conventional manner, as described above.

In an alternative embodiment, the catheters 240A,B may pass through a single suprapubic incision 252 formed on one side of the patient's abdomen, and may connect to a single external collection container 244. In this exemplary embodiment, a single valve 242 may be used to isolate the flow of urine from the catheters 240A,B to a collection container 244. As described above, seals 208A,B may be used to seal the gaps between catheters 240A,B and the ureters 206A,B. These seals 208A,B may comprise biocompatible adhesive(s), o-ring(s), fins or distal portions of the catheters that expand to press against the walls of the ureters 206A,B, as described above.

Figure 10:
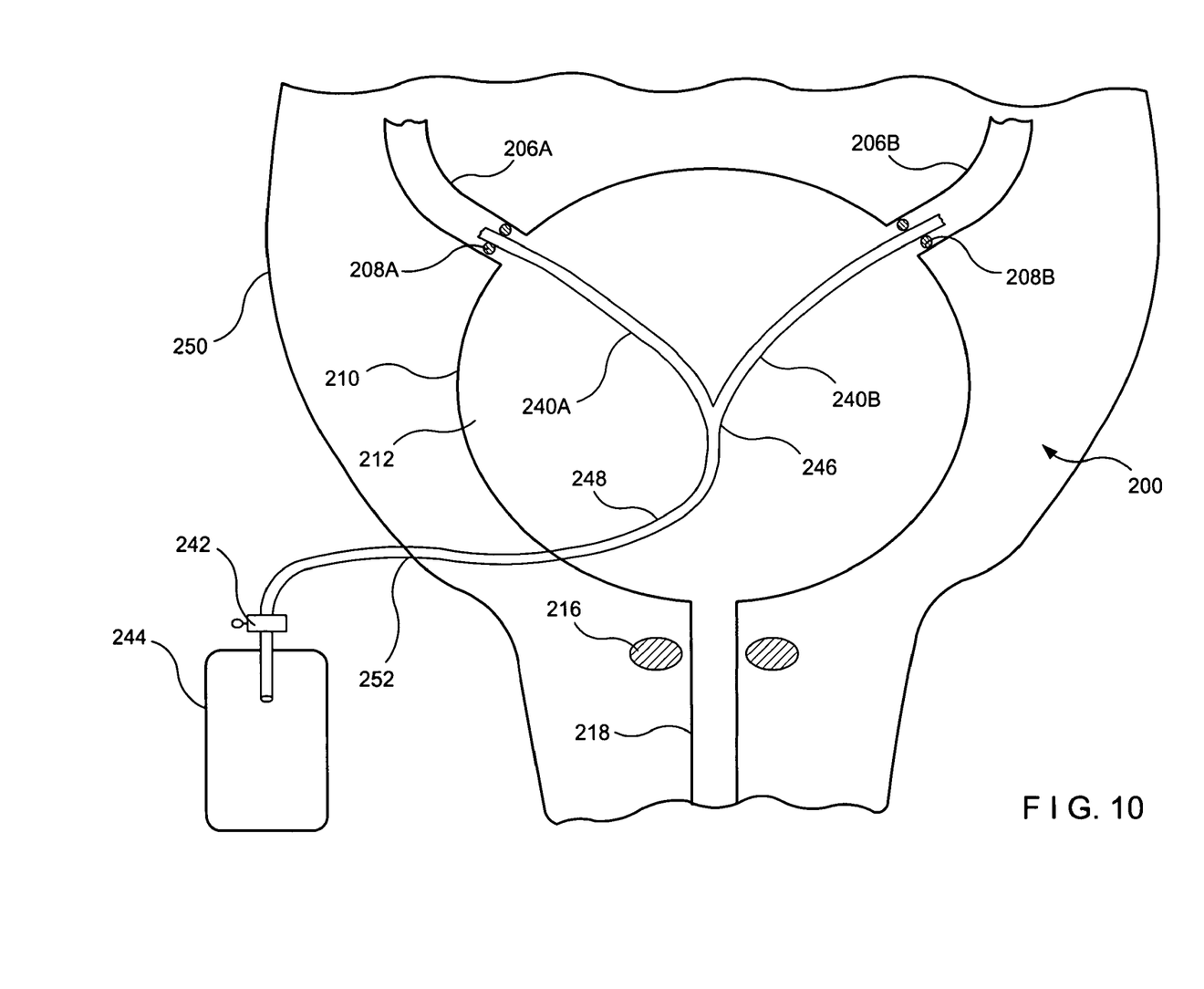
FIG. 10 is a schematic drawing showing a bladder bypass designed to fit inside a patient's urinary bladder, having two catheters which join into one exit catheter extending through a suprapubic incision in the patient's abdominal wall, according to the present invention.

A further embodiment of the device 200 is shown in FIG. 10. Two catheters 240A,B join to form a third catheter 248 within the urinary bladder 212. The third catheter 248 extends through the patient's bladder wall 210 and through an incision 252 in the abdominal wall 250 into an external collection container 244. This embodiment also eliminates irritation of the urethra 218 and the urinary sphincter 216, allows the urinary sphincter 216 to function normally and increases patient comfort. The third catheter 248 may include a valve 242 disposed between the incision 252 and the distal end of the catheter 248 to block the flow of urine while removing or replacing the urine collection container 244. The seals 208A,B used to seal the catheters 240A,B to the ureters 206A,B may be formed of biocompatible adhesive(s), o-ring(s), or catheters that expand to press against the wall of the ureters 206A,B, as described above. According to this embodiment of the invention, The catheters 240A,B and 248 may be joined at a catheter junction 246 by use of a fitting or bonding, or may be formed as a single assembly according to conventional methods. The catheters 240A,B 248 and the catheter junction 246 may be formed of materials comprising biocompatible plastics, such as vinyl, polyethylene, PVC,- silicone, ethylene vinyl acetate, and polypropylene.

Figure 11:
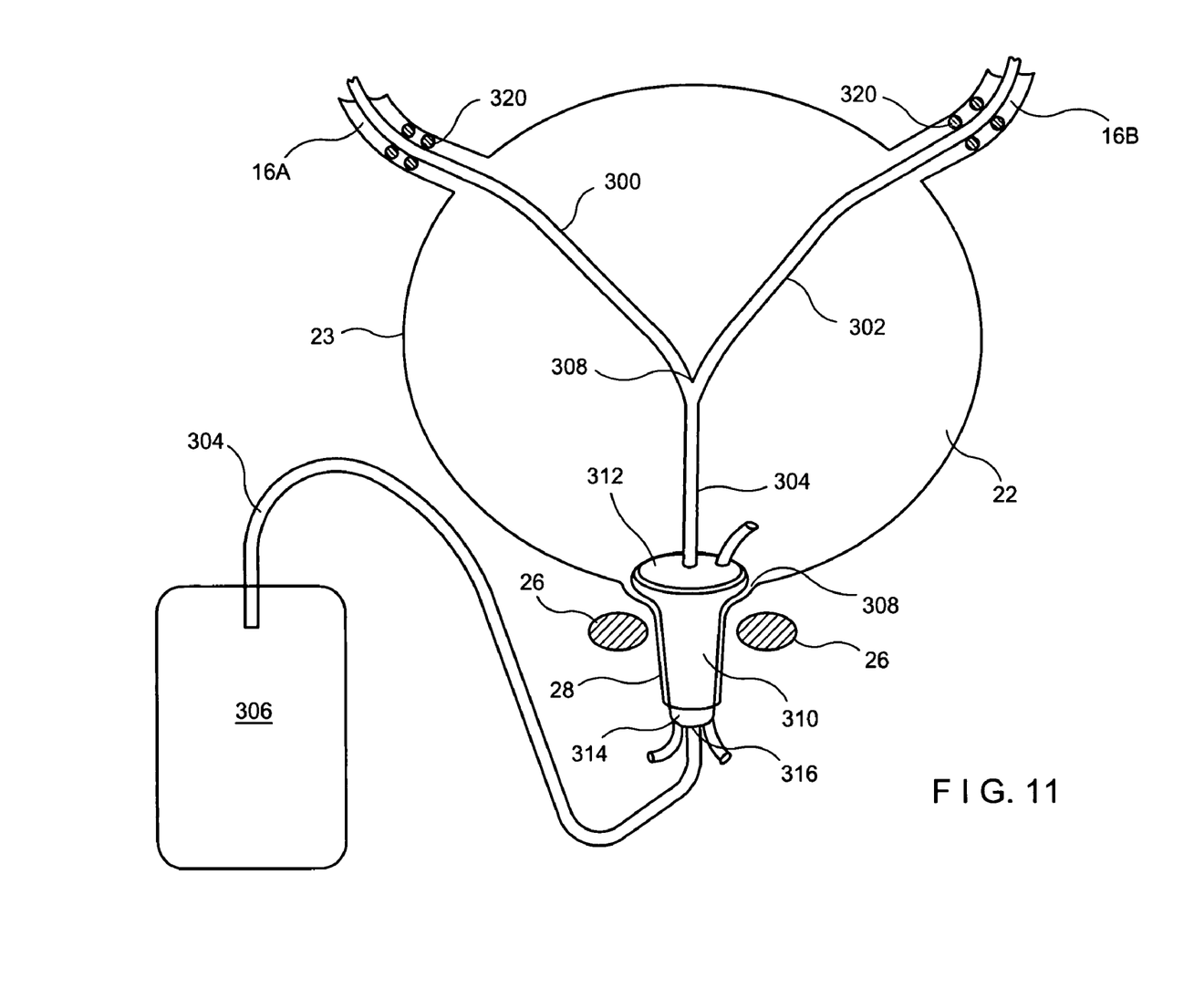
FIG. 11 is a schematic diagram showing a bladder bypass with an urethral sealing glans according to an embodiment of the present invention.

A more detailed view of a urethral sealing member used according to embodiments of the present invention is shown in FIG. 11. In this exemplary embodiment, each of a pair of catheters 300, 302 is inserted through the bladder 22 into a respective one of the ureters 16A,B. The two catheters 300, 302 are combined into a single catheter 304 at a junction 308, so that only one catheter exits the patient's body through urethra 28. In this manner, the urethra 28 is kept open only as necessary to allow passage of one catheter 304. It will be apparent to those of skill in the art that the catheters 300, 302 may also remain separate, and pass through urethra 28 independently. The outflow catheter 304 may be connected at its proximal end to a urine storage/collection device 306, such as a plastic bag or container.

As indicated above, it may be necessary in the course of therapeutic procedures to introduce a medicated fluid into the bladder 22 to topically treat the bladder wall 23. The function of the catheters 300, 302 and of the catheter 304, if present, is to prevent urine flowing from the ureters 16A, 16B from mixing with medication infused into the bladder 22. A similar purpose is carried out by the bladder liner elements described with respect to other embodiments of the invention. In addition to preventing dilution of the medication by the urine, the device according to this embodiment retains the medication within the bladder 22 for a specified dwell time selected to allow therapeutic agents in the medication to act. The sphincter 26 alone may not be sufficient to retain the medication for the desired dwell time since normal voiding functions of the bladder may occur more frequently than the required dwell time. A urethral sealing device may thus be used to provide the desired dwell time, as well as to prevent any backflow of urine into the bladder from the urethra.

An exemplary embodiment of such a urethral sealing device 310 is shown in FIG. 11, to provide a fluid tight seal to the patient's bladder 22. In this exemplary embodiment, the urethral sealing device 310 is placed within the urethra 28 such that a body 314 of the sealing device 310 extends substantially the length of the urethra 28. A distal portion 312 of the body 314 forms a plug-like sealing element which, after insertion of the sealing device 310 extends substantially within an orifice 308 to the urethra 28. A proximal portion 316 of the body 314 may extend past the orifice 308 into the bladder 22 or may be somewhat shorter, depending on the anatomy of the patient and the procedure being performed. In the exemplary embodiment, the body 314 extends across the urinary sphincter 26, from the bladder 22 to a proximal opening of the urethra to an outside the of body.

The body 314 may have a multi-piece construction which allows individual catheters to be placed independently within the bladder 22. For example, catheters 300, 302 may be placed within ureters 16A, 16B and may exit through the urethra 28 either separately or joined into an outflow catheter 304. As described above, the seals 320 prevent urine from flowing therepast into the bladder 22. As described above, the seals 320 may be blade-type or balloon seals, for example. Once the appropriate catheters are in place, the body 314 of the sealing device 310 may be assembled around the catheters and inserted into the urethra 28. Since the body 314 is disassembled prior to insertion, it is not necessary to thread the catheters into lumens of the urethral sealing device 310 as they are inserted into the bladder 22. This method of assembly simplifies the medical procedure, which can thus be carried out more rapidly and with fewer personnel. The body 314 may be formed of any soft, pliable, biocompatible material, such as, for example, silicone, latex rubber, ethylene vinyl acetate or polyethylene.

Figure 12:
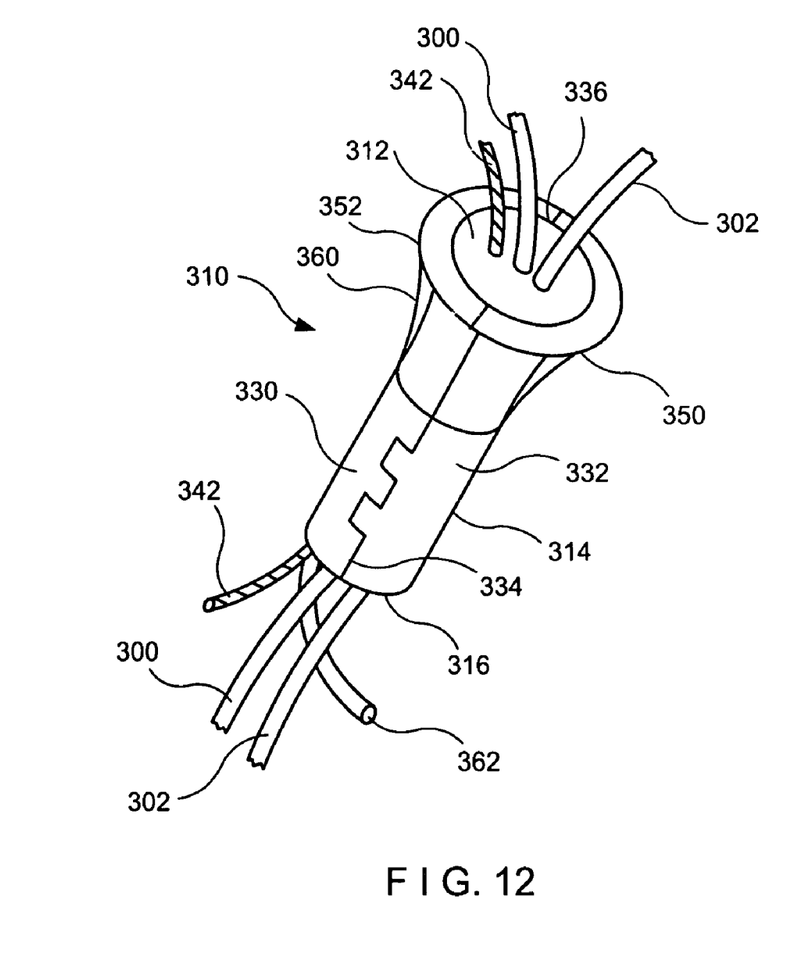
FIG. 12 is a perspective view of an urethral sealing glans in the closed configuration, according to the present invention.
Figure 13:
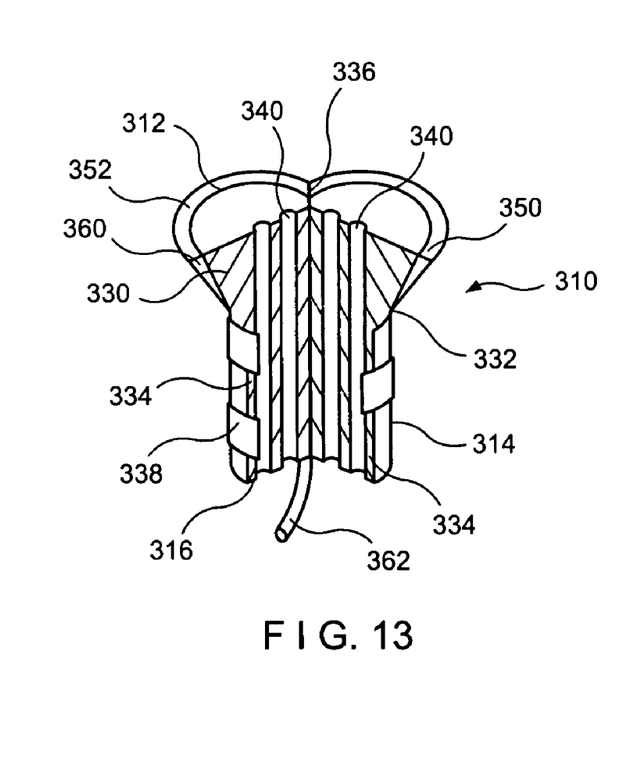
FIG. 13 is a perspective view of the urethral sealing glans shown in FIG. 12, in the open configuration.

An exemplary embodiment of the body 314 is shown in more detail in FIGS. 12 and 13. The body 314 is formed of first and second portions 330, 332 which are separable along a separation line 334. The first and second portions 330, 332 may be separable completely, or may pivot along a hinge line 336, so that the generally cylindrical body 314 splits into two portions which are substantially shaped like cylindrical half-shells when in the open configuration. Fasteners 338 may be provided as needed to retain the first and second portions 330, 332 together when the body 314 is in the closed configuration. The fasteners may be, for example, friction fasteners, interlocking fasteners, or any other type of fasteners known in the art.

Lumens are formed in the gland body 314 to let one or more outflow catheters 304 pass through the urethral sealing device 310, and extend from the bladder 22 to outside the patient's body. For example, lumens 340 may be formed by the first and second portions 330, 332, so that catheters 300, 302 may pass therethrough. Lumens 340 may be formed substantially symmetrically by the first and second portions 330, 332 or may, alternatively, be asymmetrical. Additional lumens (omitted for clarity in FIG. 13) may be formed in an analogous manner, and may be used for other purposes, such as permitting passage of a drug delivery catheter 342 therethrough to the bladder 22. The drug delivery catheter 342 may be used, for example, to infuse the medicated solution(s) into the bladder 22 after the urethral sealing element 310 has been inserted.

A sealing element 350 may be provided at the distal end of body 314, to prevent fluid from escaping through the urethra 28, around the body of the urethral sealing device 310. The sealing element 350 may comprise an enlarged portion 352 which acts as a plug in the neck 308 of the bladder 22. For example, the enlarged portion 352 may be a permanent flexible ridge disposed at the distal end of the body 314, which is adapted to seat in the urethral orifice 308 of the bladder 22. The flexible ridge of the enlarged portion 352 may comprise a gel or other suitable sealing structure. In an alternative exemplary embodiment, the sealing element 350 may comprise one or more inflatable elements, for example balloons 360, which are inflated after the body 314 has been inserted into the urethra 28 to improve the seal. The balloons 360 may be used alone or together with the ridge of the enlarged portion 352, depending on the application. An inflation port 362 connected to the balloon(s) 360 and accessible from outside the patient's body during the procedure, may also be provided. It will be apparent to those of skill in the art that the urethral sealing device 310 may be manufactured integrally with one or more of the catheters 300-304. In addition, a lubricious coating may cover all or portions of the sealing device 310.

Methods to carry out medical procedures according to the invention include treating bladder diseases by isolating urine from the urinary wall through the use of the aforementioned bladder liner and bladder bypass devices. Once the urine has been taken out of contact with the bladder wall, the patient may be treated with appropriate medications which may be applied topically directly to the diseased bladder wall. No dilution of the medication or early expulsion from the body occur according to the invention. Appropriate medications that may be used include oral medications comprising sodium pentosanpolysulfate, amitripyline, imipramine, hydroxyzine dihydrochloride, hydroxyzine hydrochloride, hyoscyamine sulfate, hyosyamine, oxybutynin chloride, flavoxate, urised, or phenazopyridine hydrochloride. According to the invention, appropriate medications which may be topically applied to the bladder wall include DMSO, heparin, sodium oxychlorosene, lidocaine, hydrocortisone sodium succinate, sodium bicarbonate, capsaicin, hyaluronic acid, silver nitrate, or bacillus of Calmette and Guerin (BCG). These medications may be instilled between the bladder liner and bladder wall to achieve topical therapy to the inner wall of the bladder. In the case of catheters used to bypass the bladder, the medications may be instilled in the bladder, and a urethral sealing device may be used in the urethra to retain the medication in place for a specified period of time.

As described above, a urethral sealing device may be used at the urethral orifice of the bladder. According to the exemplary embodiment of the present invention shown in FIGS. 12 and 13, a body 314 is separated into first and second components 330, 332 prior to insertion in the body. After one, two or more catheters have been inserted into the bladder 22 (for example catheters 300, 302 and 304), the first and second portions 330, 332 are placed around the catheters so that each catheter fits in a lumen 340 extending through the body 314. Alternatively, more than one catheter may fit in each lumen, as long as a seal is maintained. The first and second components 330, 332 are recombined and secured into an unitary element, which may be inserted into the urethra 28. A seal is then formed by a distal flexible ridge of the enlarged portion 352 of the body 314 which may be augmenter or formed separately by inflating balloons 360 through the inflation port 362.

Once the bladder liner/bypass device and the urethral sealing device 310 are in place, a medicated fluid may be introduced into the bladder 22, for example using an instillation port 342. After a desired dwell time in the bladder 22, the medicated fluid may be drained, and the urethral sealing device 310, together with the catheters may be removed. The urethral sealing device 310 may be removed following substantially the installation steps in reverse, for example by separating the gland body 314 into first and second components 330, 332. The exemplary embodiment of the invention may be used in the treatment of, for example, interstitial cystitis, bladder cancer, Hunner's ulcer, hemorrhagic cystitis, chronic cystitis, recurrent cystitis, or other bladder condition.

The present invention has been described with reference to specific exemplary embodiments. Those skilled in the art will understand that changes may be made in details, particularly in matters of shape, size, material and arrangement of parts. Accordingly, various modifications and changes may be made to the embodiments. The specifications and drawings are, therefore, to be regarded in an illustrative rather than a restrictive sense.

What is claimed is:

1. A urethral sealing device comprising:
   first and second body portions selectively attachable to one another to assume an attached configuration forming a unitary element including a first catheter lumen extending therethrough between proximal and distal ends of the unitary element wherein, when the sealing device is in an operative position, the distal end is positioned within a urinary bladder and wherein, when in a detached configuration, a first portion of a wall of the catheter lumen in the first body portion is separated from a radially opposed second portion of the wall of the catheter lumen in the second body portion; and
   a sealing element extending radially outward from the unitary element so that, when the sealing device is in the operative position, the sealing element is adapted to engage one of a wall of the urethra and a wall of the urinary bladder around an orifice at which the urethra opens into the urinary bladder to seal the urethra, wherein the unitary element further comprises a second catheter lumen extending therethrough between the proximal and distal ends of the unitary element, each one of the catheter lumen and the second catheter lumen corresponding to a respective channel in a material of the unitary element.

2. The urethral sealing device according to claim 1, further comprising a fastening element for attaching the first and second portions to one another.

3. The urethral sealing device according to claim 1, wherein the first catheter lumen extends through the unitary element substantially along a longitudinal axis thereof.

4. The urethral sealing device according to claim 1, wherein the sealing element comprises a radially expandable portion expandable to a radially enlarged configuration after insertion through the urethra.

5. The urethral sealing device according to claim 1, wherein the sealing element comprises a permanent flexible ridge adapted to seat in the orifice at which the urethra opens into the urinary bladder.

6. The urethral sealing device according to claim 1, wherein the sealing element comprises an inflatable element disposed at a distal end of the unitary element.

7. The urethral sealing device according to claim 6, wherein the unitary element further comprises an inflation port fluidly connected to the inflatable element.

8. The urethral sealing device according to claim 1, wherein the unitary element further comprises a medication delivery port fluidly connected to a medication delivery outlet at a distal end of the unitary element.

9. The urethral sealing device according to claim 1, wherein the first and second portions are formed of a semi rigid material.

10. The urethral sealing device according to claim 1, wherein the sealing element is further adapted to mechanically retain the unitary element in the urethra.

11. The urethral sealing device according to claim 9, wherein the unitary element is formed of one of silicone, latex rubber, ethylene vinyl acetate and polyethylene.

12. The urethral sealing device according to claim 1, wherein the first and second body portions mate along an interface extending substantially parallel to the first catheter lumen.

13. The urethral sealing device according to claim 12, wherein each of the first and second body portions forms a part of a wall defining the first catheter lumen.

14. The urethral sealing device according to claim 1, wherein the first and second body portions are completely separable from one another after being attached to one another.

15. A urethral sealing device comprising:
first and second body portions pivotally coupled to one another to form a unitary element including a first catheter lumen extending therethrough between proximal and distal ends of the unitary element wherein, when the sealing device is in an operative position, the distal end is positioned within a urinary bladder, the first and second body portions being pivotable between an attached position in which opposed faces of the first and second body portions mate with one another and a separated position in which the first and second body portions contact one another only at the pivotable coupling; and
a sealing element extending radially outward from the unitary element so that, when the sealing device is in the operative position, the sealing element is adapted to engage one of a wall of the urethra and a wall of the urinary bladder around an orifice at which the urethra opens into the urinary bladder to seal the urethra, wherein the unitary element further comprises a second catheter lumen extending therethrough between the proximal and distal ends of the unitary element, each one of the first catheter lumen and the second catheter lumen corresponding to a respective channel in a material of the unitary element.

16. The urethral sealing device according to claim 15, wherein the first and second body portions pivot relative to one another about an axis substantially parallel to the first catheter lumen.

* * * * *